United States Patent
Prest

(10) Patent No.: US 7,569,815 B2
(45) Date of Patent: Aug. 4, 2009

(54) GC MASS SPECTROMETRY INTERFACE AND METHOD

(75) Inventor: Harry F Prest, Santa Cruz, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 332 days.

(21) Appl. No.: 11/551,806

(22) Filed: Oct. 23, 2006

(65) Prior Publication Data
US 2008/0142701 A1 Jun. 19, 2008

(51) Int. Cl.
*G01N 30/00* (2006.01)
*H01J 49/10* (2006.01)

(52) U.S. Cl. .................. 250/288; 250/281; 250/282; 250/284; 73/23.35; 73/23.41

(58) Field of Classification Search ............ 73/23.42; 250/284, 288
See application file for complete search history.

(56) References Cited

U.S. PATENT DOCUMENTS

| | | | | |
|---|---|---|---|---|
| 3,581,465 A | * | 6/1971 | Haruki et al. .................. 95/87 |
| 4,012,199 A | * | 3/1977 | Luger .......................... 422/62 |
| 4,024,752 A | * | 5/1977 | Orlando ....................... 374/27 |
| 4,075,475 A | * | 2/1978 | Risby et al. .................. 250/282 |
| 4,211,634 A | * | 7/1980 | Bertolacini et al. ........... 208/59 |
| 4,400,532 A | * | 8/1983 | Lagow et al. ................ 560/227 |
| 4,509,855 A | * | 4/1985 | Gay ............................ 356/72 |
| 4,615,769 A | * | 10/1986 | Horigome et al. .............. 203/2 |
| 4,804,839 A | * | 2/1989 | Broadbent et al. .......... 250/288 |
| 4,814,612 A | * | 3/1989 | Vestal et al. ................. 250/288 |
| 4,948,389 A | * | 8/1990 | Klein et al. .................... 95/18 |
| 4,960,992 A | * | 10/1990 | Vestal et al. ................. 250/288 |
| 5,012,052 A | * | 4/1991 | Hayes ......................... 250/288 |
| 5,032,151 A | * | 7/1991 | Klein et al. ..................... 95/17 |
| 5,175,431 A | * | 12/1992 | Eisele et al. ................. 250/288 |
| 5,196,700 A | * | 3/1993 | Kameshima ................. 250/288 |
| 5,342,580 A | * | 8/1994 | Brenner ........................ 422/92 |
| 5,476,000 A | * | 12/1995 | Henderson et al. ......... 73/23.27 |
| 5,554,540 A | * | 9/1996 | Meng .......................... 436/153 |
| 5,665,314 A | * | 9/1997 | Berger et al. ................. 422/89 |
| 6,205,841 B1 | * | 3/2001 | Shibamoto ................. 73/23.41 |

(Continued)

*Primary Examiner*—David A. Vanore

(57) ABSTRACT

The invention provides a GC mass spectrometry system, including a column for introducing a sample into the GC mass spectrometry system, a heating source for providing heat to the sample to be separated by the column, an ion source downstream from the heating source for ionizing the sample separated by the column, the ion source having a sensor for determining the temperature of the ion source, an interface coupled to the ion source sensor and the heating source wherein the interface provides a feedback loop between the ion source sensor and the heating source and the temperature of the ion source or the heating source can be tracked and altered during data acquisition. The invention also provides an apparatus for GC mass spectrometry, including a heating source for providing heat to a column for volatizing molecules to be separated by the column; an ion source downstream from the heating source for ionizing the sample separated by the column, the ion source having a sensor for determining the temperature of the ion source; and an interface for coupling the ion source sensor to the heating source wherein the interface provides a feedback loop between the sensor of the ion source and the heating source and the temperature of the ion source and the heating source can be altered during data acquisition. Methods of heating and volatilizing samples using the GC mass spectrometry system and apparatus are also disclosed.

32 Claims, 2 Drawing Sheets

U.S. PATENT DOCUMENTS

| | | | |
|---|---|---|---|
| 6,427,522 B1 * | 8/2002 | Thomas et al. | 73/23.35 |
| 6,703,236 B2 * | 3/2004 | Atwood | 435/286.1 |
| 6,707,035 B2 * | 3/2004 | Hughey et al. | 250/288 |
| 6,815,633 B1 * | 11/2004 | Chen et al. | 219/121.54 |
| 7,140,230 B2 * | 11/2006 | Kita et al. | 73/23.34 |

* cited by examiner

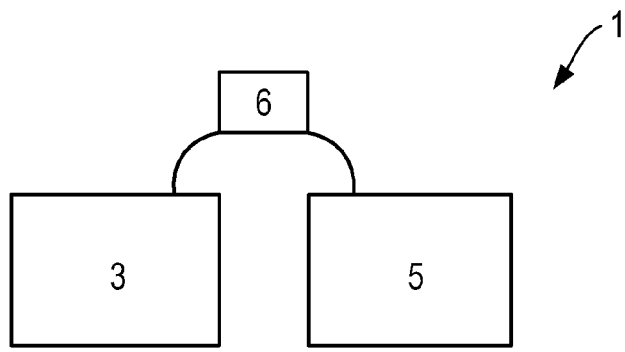
Fig. 1
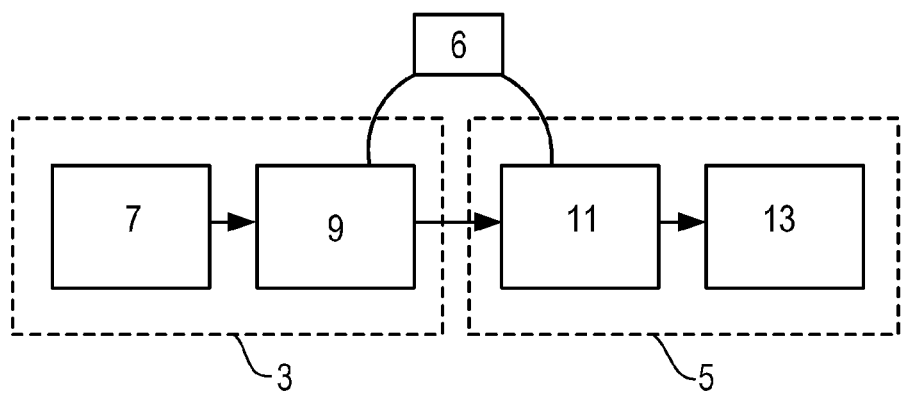
Fig. 2
| Sample Type | Heating Level | Ion Source |
|---|---|---|
| Volatile | Low | Low |
| Less Volatile | High | High |
| Standard | Low/High | Constant |
Fig. 3

GC MASS SPECTROMETRY INTERFACE AND METHOD

BACKGROUND

Typical ion sources in mass spectrometry systems are operated at a constant temperature for ease of tuning, use and issues of stability. There are many forms of sample introduction for mass spectrometric ion sources such as those involved in liquid chromatography (LC) and mechanisms of ionization (electrospray, atmospheric pressure chemical ionization, etc.) or those for samples that are more suitable to being thermal volatized due to their stability such as gas chromatography or insertion probe (for those less stable). Although these source considerations apply widely they are easiest to illustrate by the technique of gas chromatography (GC). In GC, samples are separated by their volatility and partitioning between a mobile gas (carrier) phase and a stationary phase coated on some support such as the wall of a capillary column. As the temperature of the column and carrier gas changes (usually in a heated temperature bath or oven) the distribution of the sample components between the two phases changes and a separation is possible. As the temperature changes and the components partition into the carrier and through a variety of interfaces, enter into the MS ion source where they are ionized and eventually detected. Alternatively, components can be introduced to the ion source by probe, which performs a very crude separation solely by the heating of the probe tip on which the sample resides. Higher volatility components evaporate before the less volatile. In both these scenarios, temperature is used to "move" compounds into the ion source. In LC, a change in the mobile phase composition is used to elute compounds into the ionization region. But upon entering the ion source, many compounds show different tolerances to the temperature of their new surroundings. The pattern of the ion fragmentation and the total response (signal) are dramatically influenced by the ion source temperature. Compounds that are thermally sensitive will rapidly degrade in very hot ion sources and will show a decreased response. Compounds that elute (from the GC or probe) at very high temperatures will show very poor chromatography (broad peaks non-gaussian in shape) and low response in ion sources that are too cool. As a concession to robustness in operation, ion source temperatures have usually been kept very high to prevent condensation of analytes and matrices that may compromise source cleanliness. This situation often occurs in all kinds of sources and modes of operation including and not limited to electron impact ionization, chemical ionization (positive and negative mode), electron capture negative ionization mode (ECNI), photo-ionization etc. This effect is particularly pronounced in ECNI mode.

Recognizing that analytes have differing "optimum" ion source temperatures in terms of response, spectra, etc., and that other analytical concerns exist, such as robust operation, etc., to allow for continual optimization of ion source temperature by enabling changing ion source temperatures during the analysis continues to be an ongoing problem. These and other problems have been obviated and addressed by the present invention.

SUMMARY OF THE INVENTION

The invention provides a GC mass spectrometry system, comprising a column for introducing a sample into the GC mass spectrometry system; a heating source for providing heat to the sample to be separated by the column; an ion source downstream from the heating source for ionizing the sample separated by the column, the ion source having a sensor for determining the temperature of the ion source; an interface coupled to the ion source sensor and the heating source wherein the interface provides a feedback loop between the ion source sensor and the heating source and the temperature of the ion source or the heating source can be tracked and altered during data acquisition.

The invention also provides an apparatus for GC mass spectrometry, comprising a heating source for providing heat to a column for volatizing molecules to be separated by the column; an ion source downstream from the heating source for ionizing the sample separated by the column, the ion source having a sensor for determining the temperature of the ion source; and an interface for coupling the ion source sensor to the heating source wherein the interface provides a feedback loop between the sensor of the ion source and the heating source and the temperature of the ion source and the heating source can be altered during data acquisition.

The invention also provides a method for GC mass spectrometry, comprising inputting a sample into a GC mass spectrometry system; heating the sample to a first temperature using a heating source; and introducing the sample into an ion source having a sensor that is coupled to an interface and the heating source for altering the temperature of the ion source to a second temperature.

BRIEF DESCRIPTION OF THE FIGURES

The invention is described in detail below with reference to the following figures:

FIG. 1 shows a general block diagram of the present invention.

FIG. 2 shows a second block diagram of the present invention.

FIG. 3 shows a comparison of various temperature parameters and the effect on the ion source using the various devices and modes.

DETAILED DESCRIPTION OF THE INVENTION

Figure 4A:
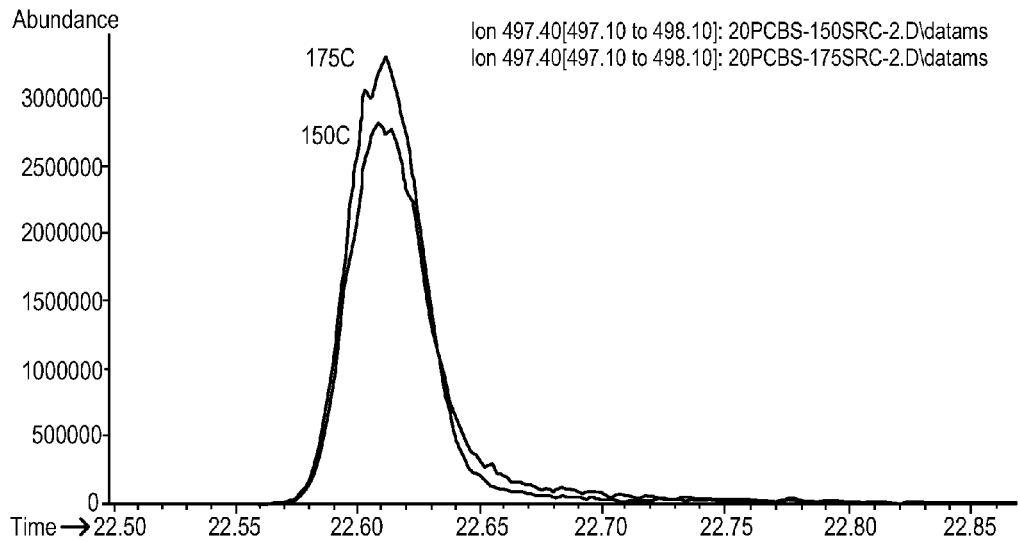
FIG. 4 shows the effects of temperature change and oven temperature on a PCB at different temperatures and capture parameters. The source is in ECNI mode.

Before describing the invention in detail, it must be noted that, as used in this specification and the appended claims, the singular forms "a," "an," and "the" include plural referents unless the context clearly dictates otherwise. Thus, for example, reference to "a housing" may include more than one "housing". Reference to "an ion source" may include more than one "ion sources".

In describing and claiming the present invention, the following terminology will be used in accordance with the definitions set out below.

The term "adjacent" means near, next to, or adjoining.

The term "column" refers to any type of analytical or preparative column that may be used for separating a sample.

The term "interface" or "mass spectrometry interface" refers to any hardware and/or software that may be used to couple a heating device to an ion source. In particular this includes any components or devices for being able to correlate temperature parameters in one device with temperature parameters of the other device.

The term "oven" refers to any device, apparatus or structure that may be used or employed to heat or vaporize analytes. The term used here is synonymous to the definition used in the art.

FIG. 1 shows a general block diagram of the present invention. The figure is not to scale and should be used for illustrative purposes only. FIG. 1 shows a gas chromatography (GC) mass spectrometry system 1. The GC mass spectrometry system comprises a gas chromatograph (GC) 3 coupled to a mass spectrometry system 5. The GC 3 is coupled to the mass spectrometry system 5 by way of interface 6. Interface 6 may comprise hardware and/or software or any materials or devices that allow for direct communication of these devices to external input.

Referring to FIG. 1-2, the GC 3 comprises a column 7 and a heating source 9 which is typically an oven or similar type device. The mass spectrometry system 5 comprises an ion source 11 and a detector 13 downstream from the ion source 11.

The GC mass spectrometry system 1 may be any system known in the art. The GC mass spectrometry system 1 may comprise various components and parts for separating and/or preparing samples using gas chromatography. It should also be noted that these components and parts need not always be closely coupled. In certain arrangements it could be imagined that the components are loosely associated or in various spatial arrangements and/or orientations.

Interface 6 is important to the invention. The interface 6 may comprise any number of hardware and/or software components that may be employed for coupling the heating source 9 to the ion source 11. For instance, the interface 6 may comprise software and/or a user interface that allows a user to input various parameters into the GC and/or mass spectrometry system 5. The interface may also comprise a sensor 15 with a feedback loop for correlating the heating source 9 and the ion source 11 (sensor 15 not shown in the drawings). The sensor 15 would typically be disposed in the ion source 11. FIG. 1-2 shows the feedback loop comprising one or more cables that connect the two devices.

Column 7 may comprise any column know in the art for separating analytes by gas chromatography. This may be both an analytical and/or preparative type column. The column 7 may be disposed or partially disposed in the heating source 9.

The heating source 9 may comprise any number of heating device known in the art. For instance, the heating source 9 may comprise an oven or similar type device. This device typically should be capable of obtaining certain high temperatures quickly to volatize compounds. One or more heating sources 9 may be employed with the present invention. The heating sources 9 may be positioned or disposed in any number of positions within the GC 3.

The ion source 11 may comprise any number of ion sources know in the art. For instance, the ion source 11 may comprise an ion trap, a triple quadrupole, a matrix assisted laser desorption ionization (MALDI), a chemical ionization (CI), and electrospray ionization (ESI), an atmospheric pressure matrix assisted laser desorption ionization (AP-MALDI) or other type of ion source that may be typically employed downstream from a GC 3.

The detector 15 may comprise any number of detectors known and used in the art for detecting ions and/or analytes. For instance, the detector 13 may comprise a time-of-flight detector, a Q-TOF detector or other similar type device. The invention should not be interpreted to be limited to these devices. Other devices known in the art may also be employed. The detector 15 may be coupled with a photomultiplier or similar type device if necessary.

The sensor 15 is important to the invention. The sensor 15 may comprise any number of sensors in the art that may be employed to detecting and/or determining temperature changes. For instance, the sensor 15 may comprise a thermocouple, thermistor or similar type device that can detect temperatures and temperature changes. The sensor 15 may comprise any number of cables, wires or other devices used for relaying the sensor calibration results or information. The sensor 15 is typically connected to the heating source 9 and the ion source 11 using a closed feedback loop.

Having described the apparatus and system of the invention, a description of the method of operation is now in order. The method for GC mass spectrometry, comprises inputting a sample into a GC mass spectrometry system; heating the sample to a first temperature using a heating source; and introducing the sample into an ion source having a sensor that is coupled to an interface and the heating source and altering the temperature of the ion source to a second temperature. Typically, this is a matching temperature or range to the first temperature of the heating source.

Figure 4B:
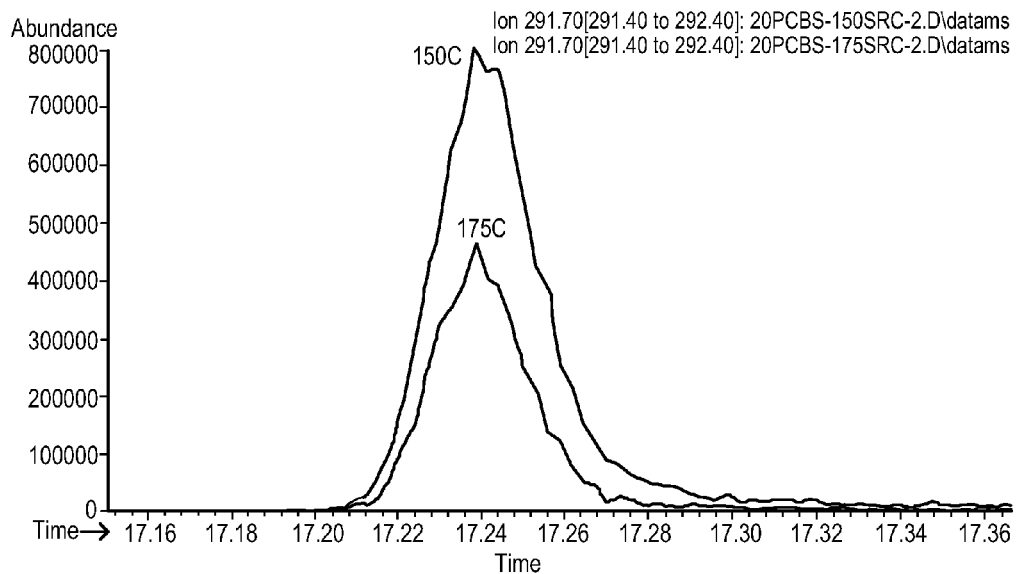

The method begins by first introducing an analyte into the GC mass spectrometry system 1. This is typically accomplished by injecting a sample into the column 7. After the sample has been injected into the column 7, the analyte travels through the column and is separated. This is accomplished by the heating source 9 which heats and volatilizes the analyte from the liquid phase to the gas phase. The heating source 9 typically heats from a low temperature to a high temperature. This is usually accomplished over a short period of time. Various analyte components and chemicals reach the gas phase at different temperatures. For instance, some compounds or analytes are more volatile than others. This affect how the compounds are separated and elute from the column. After the separation and elution, the analyte then enters the ion source 11 of the mass spectrometry system 5. As shown if FIG. 3. the various temperature parameter of the standard GC mass spectrometry system can be observed. For instance, when the heating source 9 or oven is as low temperature or high temperature based on the analyte, the ion source is kept at a constant temperature. This is the standard procedure used by most GC mass spectrometry systems, and is less than ideal. This is not ideal in providing for the best possible results. Typically, sources are mostly operated at the highest possible temperature to reduce condensation of introduced components and provide robust long term operation. This is generally true in all modes of operation including electron impact ionization, chemical ionization in positive, negative and electron capture negative ionization modes (ECNI), photoionization etc. The effects with temperature can most clearly be demonstrated in ECNI mode. FIGS. 4A and 4B shows this situation for acquisition in NCI mode at two different ion source temperatures for an early eluting and late eluting polychlorinated biphenyl (PCB). The early eluting PCB (lower panel, FIG. 4B) shows a decrease in peak height and area (lower sensitivity) at the higher source temperature and is, therefore, favored by cooler ion source temperatures. The later eluting PCB (upper level panel, FIG. 4A) shows improved chromatography and increased peak height at the higher source temperature. To accomplish this in a single acquisition the present invention proposes application of an interface 6 to help accomplish this by programming the temperature of the ion source 11 during acquisition. FIG. 3 shows how the temperature of the ion source 11 can be correlated with the heating source 9. In other words, by using an interface 6, the temperature of the ion source 11 can track the relative temperature of the heating source 9. This produces the most effective result for volatilizing and separating analytes.

We claim:

1. A GC mass spectrometry system, comprising:
   (a) a column for introducing a sample into the GC mass spectrometry system;
   (b) a heating source for providing heat to the sample to be separated by the column;
   (c) an ion source downstream from the heating source for ionizing the sample separated by the column, the ion source having a sensor for determining the temperature of the ion source;
   (d) an interface coupled to the ion source sensor and the heating source wherein the interface provides a feedback loop between the ion source sensor and the heating source and the temperature of the ion source or the heating source can be tracked and altered during data acquisition.

2. A GC mass spectrometry system as recited in claim 1, further comprising a detector for detecting the ions.

3. A GC mass spectrometry system as recited in claim 1, wherein the column is disposed in the heating source.

4. A GC mass spectrometry system as recited in claim 1, wherein the ion source further comprises a housing.

5. A GC mass spectrometry system as recited in claim 1, wherein the heating source comprises an oven.

6. A GC mass spectrometry system as recited in claim 1, wherein the sensor comprises a thermal sensor.

7. A GC mass spectrometry system as recited in claim 1, wherein the ion source sensor comprises a thermocouple.

8. A GC mass spectrometry system as recited in claim 1, wherein the heat source comprises an IR source.

9. A GC mass spectrometry system as recited in claim 3, wherein the housing comprises a metal.

10. A GC mass spectrometry system as recited in claim 3, wherein the housing comprises an inert material.

11. A GC mass spectrometry system as recited in claim 3, wherein the housing comprises a low mass material.

12. A GC mass spectrometry system as recited in claim 1, wherein the interface comprises system software.

13. A GC mass spectrometry system as recited in claim 11, wherein the interface comprises a user interface for inputting data.

14. A GC mass spectrometry system as recited in claim 1, wherein the heating source can be temperature ramped.

15. A GC mass spectrometry system as recited in claim 1, wherein when the heating source is at a high temperature the ion source is at a high relative temperature.

16. A GC mass spectrometry system as recited in claim 1, wherein when the heating source is at a low temperature the ion source is at a low temperature.

17. An apparatus for GC mass spectrometry, comprising:
   (a) a heating source for providing heat to a column for volatizing molecules to be separated by the column;
   (b) an ion source downstream from the heating source for ionizing the sample separated by the column, the ion source having a sensor for determining the temperature of the ion source; and
   (c) an interface for coupling the ion source sensor to the heating source wherein the interface provides a feedback loop between the sensor of the ion source and the heating source and the temperature of the ion source and the heating source can be altered during data acquisition.

18. An apparatus for GC mass spectrometry as recited in claim 17, further comprising a detector for detecting the ions.

19. An apparatus for GC mass spectrometry as recited in claim 17, wherein the ion source further comprises a housing.

20. An apparatus for GC mass spectrometry as recited in claim 17, wherein the heating source comprises an oven.

21. An apparatus for GC mass spectrometry as recited in claim 17, wherein the sensor comprises a thermal sensor.

22. An apparatus for GC mass spectrometry as recited in claim 17, wherein the ion source sensor comprises a thermocouple.

23. An apparatus for GC mass spectrometry as recited in claim 17, wherein the heat source comprises an IR source.

24. An apparatus for GC mass spectrometry as recited in claim 19, wherein the housing comprises a metal.

25. An apparatus for GC mass spectrometry as recited in claim 19, wherein the housing comprises an inert material.

26. An apparatus for GC mass spectrometry as recited in claim 19, wherein the housing comprises a low mass material.

27. An apparatus GC mass spectrometry as recited in claim 17, wherein the interface comprises system software.

28. An apparatus for GC mass spectrometry as recited in claim 17, wherein the interface comprises a user interface for inputting data.

29. An apparatus for GC mass spectrometry as recited in claim 17, wherein the heating source can be temperature ramped.

30. An apparatus for GC mass spectrometry as recited in claim 17, wherein when the heating source is at a high temperature the ion source is at a high relative temperature.

31. An apparatus for GC mass spectrometry as recited in claim 17, wherein when the heating source is at a low temperature the ion source is at a low temperature.

32. A method for GC mass spectrometry, comprising:
   (a) inputting a sample into a GC mass spectrometry system;
   (b) heating the sample to a first temperature using a heating source; and
   (c) introducing the sample into an ion source having a sensor that is coupled to an interface and the heating source for altering the temperature of the ion source to a second temperature.

* * * * *